United States Patent [19]
Terada

[11] Patent Number: 4,570,495
[45] Date of Patent: Feb. 18, 1986

[54] APPARATUS FOR DRAWING LIQUID SAMPLES INTO A LIQUID TESTING MACHINE

[75] Inventor: Kunio Terada, Kyoto, Japan

[73] Assignee: Horiba, Ltd., Kyoto, Japan

[21] Appl. No.: 612,028

[22] Filed: May 18, 1984

[30] Foreign Application Priority Data

Jun. 4, 1983 [JP] Japan .............................. 58-86890[U]

[51] Int. Cl.⁴ ........................ B07L 3/02; G07N 35/06
[52] U.S. Cl. ................................ 73/864.25; 141/130; 422/63; 422/100
[58] Field of Search ........... 73/864.23, 864.24, 864.25, 73/864.91; 422/63, 100; 141/130

[56] References Cited

U.S. PATENT DOCUMENTS

| | | | |
|---|---|---|---|
| 3,748,911 | 7/1973 | Rousselet et al. ................ | 73/864.25 |
| 3,853,008 | 12/1974 | Hoffa et al. ...................... | 73/864.25 |
| 3,853,011 | 12/1974 | Baumann ......................... | 73/864.24 |
| 3,949,615 | 4/1976 | Stein et al. ...................... | 73/864.24 |
| 4,022,067 | 5/1977 | Murányi et al. ................. | 73/864.25 |
| 4,343,766 | 8/1982 | Sisti et al. ............................ | 422/63 |

FOREIGN PATENT DOCUMENTS 98361  7/1980  Japan .................................. 422/100

*Primary Examiner*—David L. Lacey
*Attorney, Agent, or Firm*—Wenderoth, Lind & Ponack

[57] ABSTRACT

An apparatus for drawing liquid samples and the like into an analytical testing machine, which includes a vertically extending guide rail fixed to a base, a movable support member slidably mounted on the guide rail for movement between an upper position and a lower position, a stopper for blocking movement of the movable support member above the upper position, an arm holding a probe at an end thereof and pivotally mounted to the movable support member at the other end, an arciform guide projecting from a pivot member so as to engage the upper surface of a fixed support member when the movable support member in its upper position and the arm is pivoted upward, and a detent mechanism fixed to the movable support member and elastically engageable with the pivot member for releasably holding the arm in a first predetermined inclination. When the movable support member is in its upper position, the arm is pivotable upward to a second predetermined inclination so as to bring the arciform guide into a position where it is vertically supported by the fixed support member.

11 Claims, 4 Drawing Figures

APPARATUS FOR DRAWING LIQUID SAMPLES INTO A LIQUID TESTING MACHINE

BACKGROUND OF THE INVENTION

1. Field of the Invention

The present invention relates to a means for drawing samples of blood or the like from a test tube by suction into a testing machine for analyzing electrolytes in blood, and for drawing up washings from a washing cup to wash the line leading to the testing machine after the completion of the analysis.

2. Description of the Prior Art

Previously, in the use of such machines for analyzing electrolytes in blood or the like, a probe has been selectively inserted by hand into a test tube or a washing cup, or the test tube or washing cup has been selectively moved to the place of a probe fixedly mounted on the machine, and then a suction pump has been switched on in order to draw samples or washing into the testing machine.

However, the prior art has such disadvantages that, for example, in the case of the testing of blood, it is necessary to wash the line leading from the probe to the testing machine after every analysis of a sample. Thus, in the case of the analysis of a large number of samples, not only must a probe be repeatedly inserted into and taken out of a test tube and a washing cup while a person confirms the relative location of the test cup and the washing cup, but also, the probe or test tube and washing cup must be continuously held by hand during the suctioning process for every sample and washing drawn up through the probe, thereby increasing the cost of labor in the analytical operation and tiring the person performing such labor.

BRIEF SUMMARY OF THE INVENTION

It is an object of the present invention to eliminate the entirely manual positioning and holding of a probe or the like to efficiently carry out the analytical liquid testing operation.

An apparatus for drawing up samples and the like by suction according to the present invention includes a movable support member which is slidable up and down along a vertically extending guide rail. A stopper is provided for blocking upward movement of the movable support member at a predetermined upper position. An arm holding a probe at one end is pivotally mounted to the movable support member by a pivot member for pivotal movement about a horizontal axis. An arciform guide is provided on the pivot member so as be engagable with a fixed support member to be vertically supported thereby when the movable support member is at the upper position and the arm is pivoted upward. A detent mechanism is mounted on the movable support member and is elastically engagable with the pivot member to releasably hold the arm in a first predetermined inclination. The arm is pivotable upward from the first predetermined inclination to a second predetermined inclination against the elastic force of the detent mechanism so as to bring the arciform guide into a position where it is vertically supported by the fixed support member when the movable support member in its upper position.

With such an apparatus, a probe can be inserted into and removed from a washing cup or a test tube merely by causing the movable support member to move up and down after locating the washing cup or test tube in positions where the probe is naturally introduced thereinto, by moving the movable support member downward with the arm in its first predetermined inclination, or upward and then pivoting the arm into its second predetermined inclination.

Accordingly, a probe can be introduced into and removed from either a washing cup or a test tube without confirming the relative location thereof, and further, the drawing upward of either of washings or samples can be completed without holding either the washing cup or the test tube by hand. Thus, the invention is capable of substantially reducing the amount of labor and fatigue in similar efforts with conventional means for carrying out the analytical operations. In addition, since the lower end of the probe can be projected outwardly at the upper position of the movable support member, the test tube can be introduced to and removed from the probe in an inclined posture in a wide space, so that the operation is easily performed.

BRIEF DESCRIPTION OF THE DRAWINGS

These and other aspects of the invention will be better understood from the following detailed description of the preferred embodiments when taken with the accompanying drawings in which.

DESCRIPTION OF THE PREFERRED EMBODIMENTS

Figure 1:
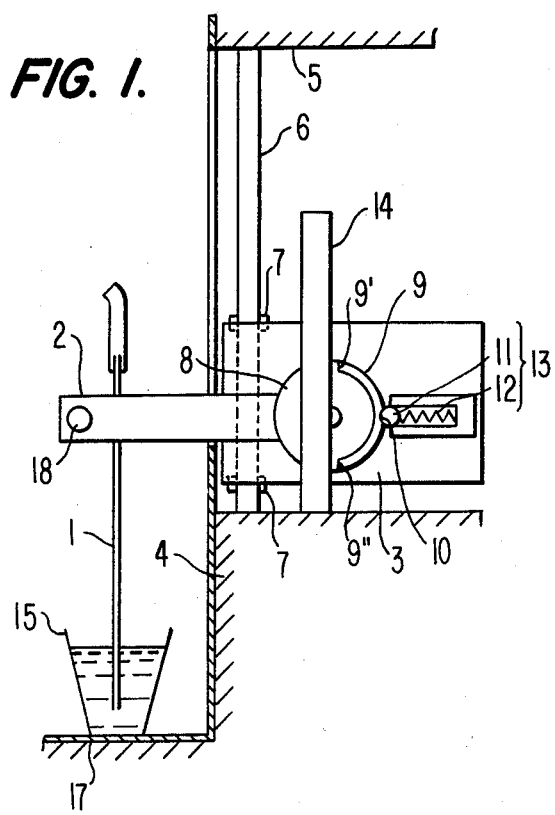
FIG. 1 is a side view of a preferred embodiment of the invention, in a state in which a movable support member is in a lower position for drawing washings from a cup.

The preferred embodiments of the present invention will be described below with reference to the drawings.

Referring now to the drawings, a means for selectively drawing up with a suction pump (not shown in the drawings) samples such as blood, and washings, comprises a probe 1 held by an arm 2 and connected with one of various kinds of analytical instruments or machines (not shown in the drawings) such as an apparatus for analyzing electrolytes in blood. The arm 2 is pivotally mounted at one end on a movable support member 3, and support member 3 is slidably mounted on a guide rail 6 extending from a fixedly mounted stand (base) to an upper fixing member or "stopper" 5 through a pair of vertically aligned bearings 7.

The support member 3 includes a horizontal axle P. The arm 2 is provided with an operating lever 18 projecting from one end thereof and a circular plate 8 fixedly mounted thereon at the other. Circular plate 8 is mounted on the movable support member 3 so as to be pivotable about the horizontal axle P. The circular plate 8 is provided with an arciform guide 9 protruding outwardly from the plane thereof. Arciform guide 9 has end surfaces 9' and 9" and an indented portion 10 formed at an appointed position midway between end surfaces 9' and 9" in a circumferential direction of the arciform guide 9. The support member 3 is provided with a ball detent mechanism 13 consisting of a cylinder having an open end, a ball 11 which is movable into and out of the indented portion 10 through the open end of the cylinder, and a spring 12 for pressing the ball 11 to the side into the indented portion 10. Ball detent mechanism 13 permits probe 1 to be held against pivotal movement in a vertical orientation by introducing ball 11 into the indented portion 10.

The base 4 is provided with a columnar fixing guide 14 fixedly upstanding therefrom in parallel to the guide rail and along both end surfaces 9' and 9" of arciform guide 9 in the diametrical direction thereof, so that arm 2 may move upwardly and downwardly in such a posture that the probe 1 turns to a substantially vertical direction by engagement of end surfaces 9' and 9" of arciform guide 9 with guide 14 even if ball 11 were removed from indented portion 10 against the actuating force of spring 12.

Figure 2:
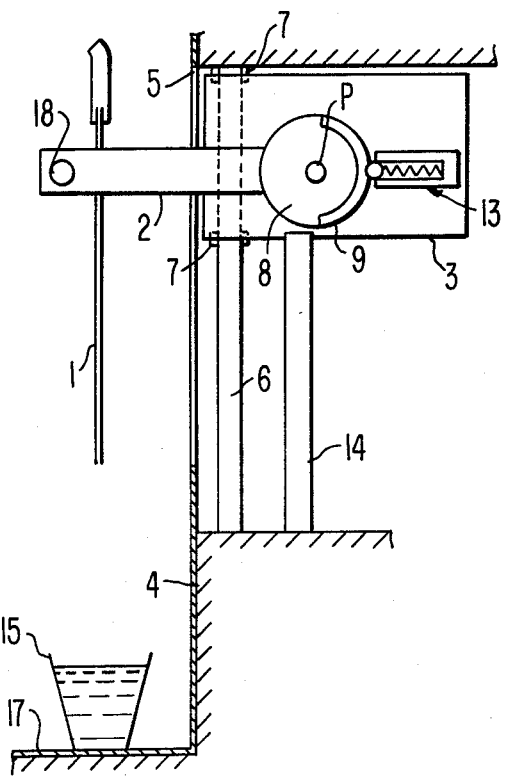
FIG. 2 is a side view thereof in a state in which the movable support member is in an upper position thereof.
Figure 3:
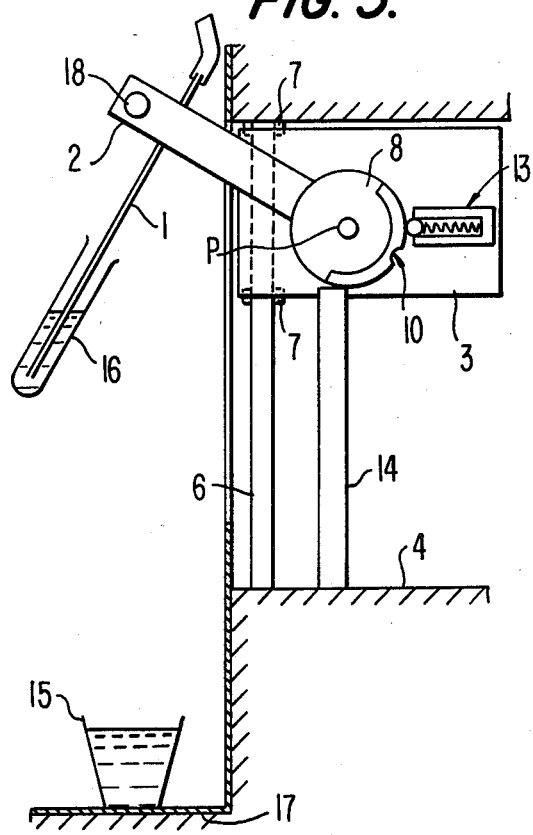
FIG. 3 is a side view thereof in which an arm is swung into a position for drawing samples from a test tube.

The height of guide 14 is selected so that the upper end surface thereof is located slightly below the lower end of arciform guide 9 when support member 3 is at its maximum height butted up against the upper fixing member 5 with its uppermost bearing 7, as illustrated in FIG. 2. In this state, arm 2 may be guided and pivoted with the arciform guide 9 resting on the upper end of guide 14 so as to change the posture of the probe 1 to an inclined one with the lower end thereof kept at a distance from the guide rail 6 as illustrated in FIG. 3.

Fixed to the base 4 below probe 1 is a stand 17 for placing washing cup 15 thereon.

The apparatus is used to repeatedly draw samples and washings. In use, washing cup 15 containing washing fluid is placed on stand 17 and probe 1 is brought down by means of the lever 18 into washing cup 15 as shown in FIG. 1. Washings are then drawn from cup 15 to rinse the line leading to the testing machine by switching on the suction pump.

After the line has been rinsed the suction pump is switched off and lever 18 is lifted to raise probe 1 from the cup 15 and simultaneously lift support member 3. As a result, as shown in FIG. 2, the arciform guide is positioned above the upper surface of guide 14 with support member 3 engaging upper fixing member 5. As shown in FIG. 3, further upward force on lever 18 causes arm 2 to pivot until it engages the side edge of upper fixing member 5, thereby changing the posture of probe 1 to an inclined one with a predetermined inclination. In this position, probe 1 is introduced into a test tube 16 and the suction pump is switched on to draw the sample contained in the test tube 16 into the analytical testing apparatus for analysis.

After completion of the suction of samples into the analytical testing apparatus, the switch is turned off and simultaneously lever 18 is pushed downwardly to dissengage arciform guide 9 from the upper end surface of guide 14 as shown in FIG. 2. Subsequently, the support member 3 is brought down from the position shown in FIG. 2 to the position shown in FIG. 1. Washings and samples are alternatively drawn through the probe 1 by repeating the above described operations.

Figure 4:
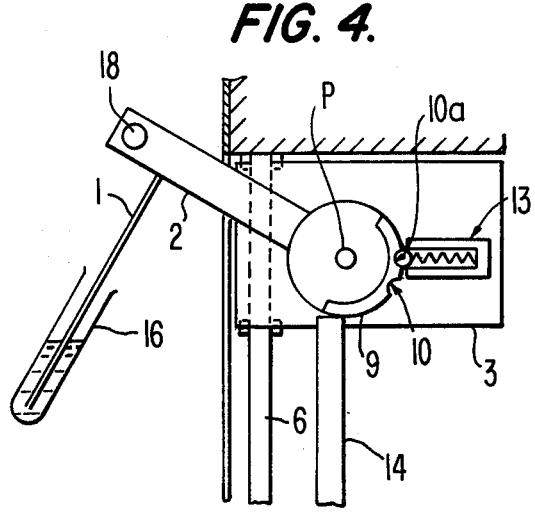
FIG. 4 is a side view of the principle parts of another preferred embodiment of the present invention.

Referring now to FIG. 4, there is shown another preferred embodiment of the present invention in which a second indented portion 10a, in addition to indented portion 10, is provided for introducing the ball 11 thereinto at an appointed position at the circumference of arciform guide 9. Indented portion 10a serves to maintain probe 1 in a stabilized inclined posture as shown in FIG. 4.

Many other variations in the structure of the apparatus can be utilized. For example, the base 4 may be formed integrally with the upper fixing member 5 by means of a casing or the like, or the base 4 and upper fixing member 5 may be separately mounted on separate supports.

In addition, in place of the upper fixing member 5, a plate member may be mounted on the upper end of guide rail 6 to limit the upward movement of support member 3.

The guide 14 need not be columnar in shape. For example, a horizontally projecting plate member may be located at the position corresponding to the top surface of guide 14 so as to support arciform guide 9 only when arm 2 is rotated at the uppermost position thereof.

Further, a limit switch of the type which is normally open may be connected with base 4 and upper fixing member 5, respectively, in parallel in order to be closed and automatically start the suction pump as soon as movable support member 3 is raised or lowered to the appointed positions respectively shown in FIGS. 1 and 3, for drawing of washings and samples through the probe 1. With such a limit switch, it would therefore not be required to manually operate a switch to start the suction pump in order to repeat the suction of samples and the suction of washings through the probe 1. Such a modified apparatus would therefore be capable of promoting still more efficient analytical operations.

What is claimed is:

1. An apparatus for drawing liquid samples and the like, comprising:

a base;

a vertically extending guide rail fixed to said base;

a movable support member slidably mounted on said guide rail for vertical movement therealong between a lower position and an upper position above said lower position;

means for blocking movement of said movable support member above said upper position;

a probe for guiding therethrough the samples or the like;

an arm holding said probe at one end thereof;

a pivot member, including an arciform guide, fixed to the other end of said arm, pivotally mounting said arm to said movable support member for pivotal movement about a horizontal axis;

a fixed support member positioned and arranged to engage said arciform guide so as to vertically support said arm when said movable support member is at said upper position and said arm is pivoted upward; and means, including a detent mechanism vertically movable with said movable support member and elastically engagable with said pivot member, for releasably holding said arm in a first predetermined inclination;

said arm being positioned and arranged so as to be pivotable upward in a plane from said first predetermined inclination toward a second predetermined inclination against the elastic force of said detent mechanism acting on said pivot member so as to bring said arciform guide into a position where it is vertically supported by said fixed support member, when said movable support member is in said upper position.

2. An apparatus as in claim 1, wherein said pivot member is located in said plane, said arciform guide protruding outwardly from said plane, said fixed support member comprising a support surface in a position which is entirely outward of said plane, is horizontally spaced from said arciform guide when said arm is in said first predetermined inclination, and is directly below said arciform guide when said movable support member is in said upper position and said arm is in said second predetermined inclination.

3. An apparatus as in claim 2, wherein said fixed support member comprises a columnar guide member extending upward from said base, said columnar guide member having an upper surface forming said support surface, said upper surface slidably supporting said arciform guide when said arm is pivoted toward said second predetermined inclination while said movable support member is in said upper position, said arciform guide having opposite ends which terminate at locations which move vertically along and in sliding engagement with said columnar guide member when said movable support member is moved between said upper and lower positions.

4. An apparatus as in claim 2, wherein said releasably holding means includes a cylinder mounted to said movable support member and having an open front end opening toward said arciform guide, a spring in said cylinder, a ball in said cylinder urged partially out of said open front end by said spring, and a first indentation in said arciform guide positioned so as to be aligned with said open end when said arm is in said first predetermined inclination, for receiving said ball therein to resist pivotal movement of said arciform guide and said arm when said arm is in said first predetermined inclination, said spring urging said ball partially out of said open front end into said first indentation.

5. An apparatus as in claim 4, wherein said arciform guide has a second indentation therein circumferentially spaced from said first indentation positioned so as to be aligned with said open front end when said arm is in said second predetermined inclination, for receiving said ball therein when said arm is in said second predetermined position to resist pivotal movement of said arciform guide and said arm, said spring urging said ball partially out of said open front end into said second indentation.

6. An apparatus as in claim 1, wherein said releasably holding means is constructed and arranged such that said first predetermined inclination is horizontal, and said arm extends upwardly from said other end to said one end in said second predetermined inclination.

7. An apparatus as in claim 6, wherein said probe is fixed to said arm so as to extend vertically downward therefrom when said arm extends horizontally, said apparatus further comprising a cup stand for supporting a cup, fixed to said base below said one end of said arm, so that the cup receives said probe therein when said movable support member is moved to said lower position.

8. An apparatus as in claim 1, wherein said arm comprises an operating lever extending outwardly from said plane at said one end.

9. An apparatus as in claim 1, wherein said movement blocking means comprises an upper fixing member mounted to said base above said fixed support member so as to block upward movement of said movable support member above said upper position.

10. An apparatus as in claim 9, further comprising means for blocking pivotal movement of said arm above said second predetermined inclination.

11. An apparatus as in claim 9, wherein said upper fixing member includes an edge positioned and arranged to block pivotal movement of said arm above said second predetermined inclination.

* * * * *